United States Patent [19]

Yoshino et al.

[11] Patent Number: 4,711,540
[45] Date of Patent: Dec. 8, 1987

[54] EYE DISEASE INSPECTING INSTRUMENT

[75] Inventors: Hisakazu Yoshino, Tokyo; Shinichi Nishimura, Ageo; Kazuyuki Sasaki, Kanazawa, all of Japan

[73] Assignee: Tokyo Kogaku Kikai Kabushiki Kaisha, Tokyo, Japan

[21] Appl. No.: 688,586

[22] Filed: Jan. 3, 1985

[30] Foreign Application Priority Data

| Jan. 4, 1984 [JP] | Japan | 59-178 |
| Jan. 4, 1984 [JP] | Japan | 59-179 |
| Aug. 10, 1984 [JP] | Japan | 59-167662 |
| Aug. 10, 1984 [JP] | Japan | 59-167663 |

[51] Int. Cl.⁴ .................................. A61B 3/10
[52] U.S. Cl. .......................... 351/214; 351/205
[58] Field of Search .................. 351/205, 214, 221

[56] References Cited

U.S. PATENT DOCUMENTS 4,171,877 10/1979 Karasawa et al. ............ 351/214 X
4,523,821 6/1985 Lang et al. ...................... 351/214

FOREIGN PATENT DOCUMENTS 53-103686 9/1978 Japan.

OTHER PUBLICATIONS

Nippon Ganka Gakkai Zasshi (Japan Ophthalmologic Institute Journal), vol. 62, No. 4, Apr. 10, 1958, pp. 22-(380)-26-(384).
Rinsho Ganka, vol. 32, No. 6, (Jun. 1978), pp. 973-976, "Retroillumination Photography of Cataractous Lens".

Primary Examiner—Rodney B. Bovernick
Attorney, Agent, or Firm—Brumbaugh, Graves, Donohue & Raymond

[57] ABSTRACT

An eye disease inspection instrument comprising a slit light projection optical system for projecting a slit light along a projecting optical axis to a patient's eye, a first optical system for observing a crystalline lens of the patient's eye at a section which is being illuminated by the slit light, a second optical system including an objective lens having an objective optical axis substantially coaxial with respect to the projecting optical axis for performing an observation under a retroillumination method.

17 Claims, 12 Drawing Figures

EYE DISEASE INSPECTING INSTRUMENT

BACKGROUND OF THE INVENTION

1. Field of the Invention

The present invention relates to disease detecting means for human eyes and more particularly to inspection instruments for human crystalline lenses. More specifically, the present invention pertains to an inspection instrument which makes possible observations of optical sections of a crystalline lens as well as observations under a retroillumination method so that cataract and its progress can readily be detected.

2. Description of the Prior Art

Conventional eye disease inspection instruments include a crystalline section observation instrument in which a thin planar pattern of light or a so-called slit light is projected through a crystalline lens and the illuminated section of the crystalline lens is observed in a direction having an angle with respect to the illuminated section. It has also been known to arrange the image plane of the observation optical system so that an extension of the image plane contains a line of intersection between the plane of the slit light and a principal plane of the imaging optical system of the observation optical system. With this optical arrangement, it becomes possible to have the crystalline section image focused throughout the section and an example of such optical arrangement is disclosed for public inspection on Sept. 9, 1978 by Japanese Patent Public Disclosure No. 53-103686 corresponding to Patent Application No. 52-18511, filed on Feb. 21, 1977. The conventional instrument is considered as being advantageous in that the image of the crystalline section can be performed in a focused condition throughout the section. However, inconveniences have been encountered in that each observation can be performed with respect to one section only so that a lot of time is required to perform observations throughout the eye. Thus, the conventional instruments have been very inconvenient in making an accurate judgement of the location and the progress of the disease in an inspection of, for example, cataract.

As a method for observing an overall image of a crystalline lens, it has been known to project a slit light to a patient's eye and illuminate the crystalline lens by light beams which are reflections at the eye fundus of the projected slit light. The method is known as a retroillumination from an eye fundus and an instrument for performing the retroillumination method may include a polarizer in the illuminating optical system and an analyzer in the observing optical system. Examples of such optical arrangement are disclosed in Japanese publications "Rinsho Ganka (Clinical Ophthalmology)" Vol. 32, No. 6 (June 1978) and "Nippon Ganka Gakkai Zasshi (Japan Ophthalmologic Institute Journal)", Vol. 62, No. 4, Apr. 10, 1958, page 22-(380)-26(384). It has however been recognized that the conventional instrument for the retroillumination method cannot be used for the purpose of recording and measurement, since assurance cannot be made in respect of stabilities of direction of the slit illumination beams, of the quantity of illumination light, of the direction of observation and of the position of observation.

OBJECTS OF THE INVENTION

It is an object of the present invention to provide an eye disease inspection instrument which can perform an observation of a section of a crystalline lens as well as an overall observation of the crystalline lens under a retroillumination method.

Another object of the present invention is to provide an eye disease inspection instrument in which results of observations can be recorded.

A further object of the present invention is to provide an eye disease inspection instrument which is convenient for inspections of a progress of disease.

SUMMARY OF THE INVENTION

In order to accomplish the above and other objects, the eye disease inspection instrument in accordance with the present invention comprises slit light projection means for projecting a slit light along a projecting optical axis to a patient's eye, a first optical system for observing a crystalline lens of the patient's eye at a section which is being illuminated by the slit light, a second optical system including objective lens means having an objective optical axis substantially coaxial with respect to the projecting optical axis for performing an observation under a retroillumination method. According to a preferable aspect of the present invention, the second optical system is provided at a focal point with a reticle having a mark for designating a position of incidence of the slit light to the crystalline lens. It is preferable that the reticle be arranged substantially coaxially with the projecting optical axis of the slit light projecting means. The second optical system may include eye lens means which is preferably arranged coaxially with the projecting optical axis. It is further preferable that the slit light projecting means, the first optical system and the reticle of the second optical system are rotatable about the slit projecting optical axis.

In a further preferable aspect of the present invention, the eye lens means is commonly used for the first and second optical systems so that the observation can be carried out through the common eye lens means by selecting one of the first and second optical systems. In order to prevent harmful reflection at the cornea of the patient's eye from being admitted to the observation optical systems, it is preferred to provide the slit light projecting means with a polarizer and the second optical system with a second polarizer having a polarizing axis perpendicular to that of the first polarizer. It is further preferable that the second polarizer be provided retractably from the optical path of the second optical system.

In order that the present invention be understood more clearly, descriptions will now be made with respect to an embodiment making reference to the accompanying drawings.

BRIEF DESCRIPTION OF THE DRAWING

FIG. 8b is a sectional view of the reticle shown in FIG. 8a.

DESCRIPTION OF THE PREFERRED EMBODIMENT

General Arrangements

Figure 1:
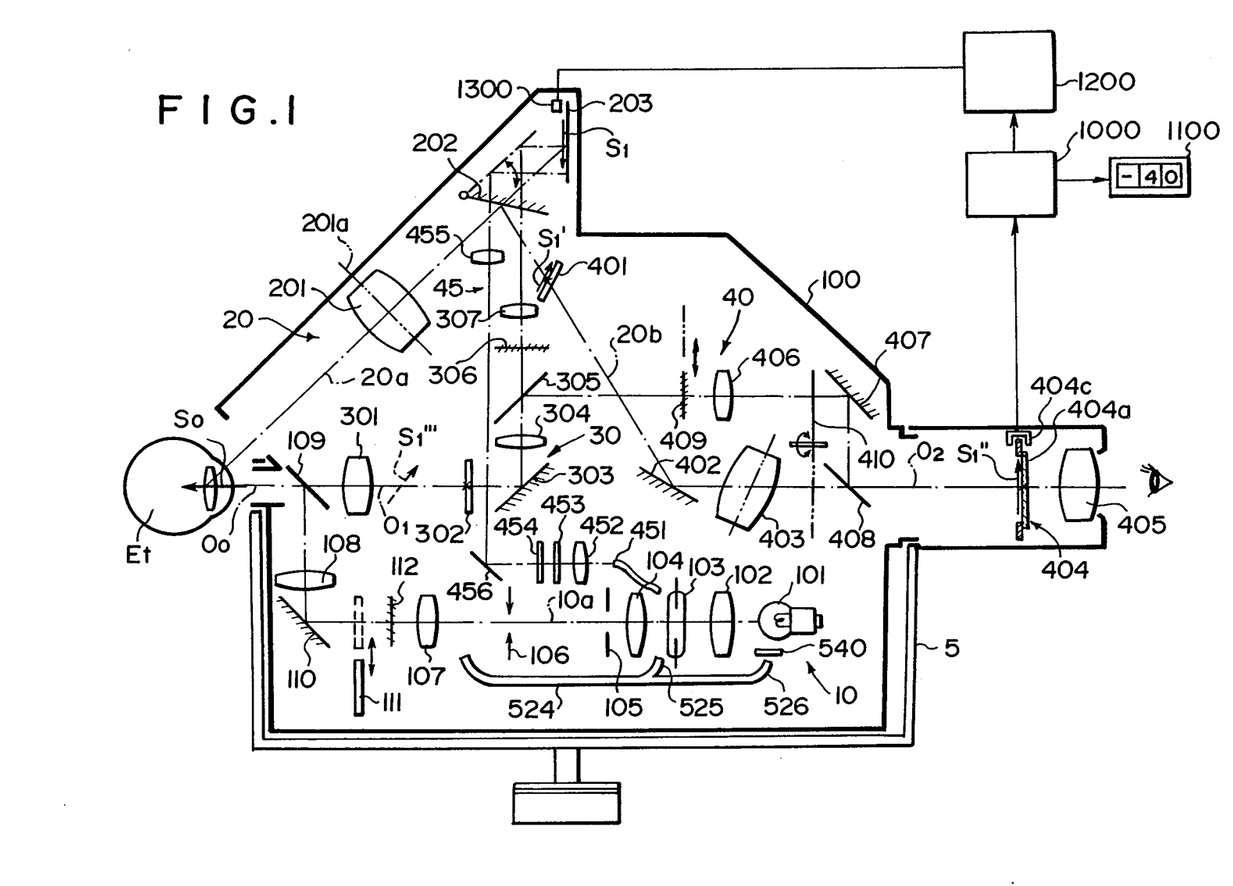
FIG. 1 is a diagrammatical sectional view of an eye disease inspection instrument in accordance with one embodiment of the present invention.

Referring to the drawings, particularly to FIG. 1, the eye disease inspection instrument embodying the present invention includes a slit light projecting optical system 10, a crystalline section photographing optical system 20, a retroillumination photographing optical system 30, an observing optical system 40 and a density chart photographing system 45 which are contained in a housing 100.

Slit Light Projecting Optical System 10

The slit light projecting optical system 10 includes a light source system comprised of an observation light source such as a tungsten lamp 101 and a photographing light source such as a xenon lamp 103. A condenser lens 102 is provided between the lamps 101 and 103. In order to direct the beams of light from the light source along a projecting optical path 10a, there is provided a condenser lens 104. Along the optical path 10a, there are further provided an aperture 105 and a slit-aperture 106. The slit aperture 106 functions to pass the light beams from the light source in the shape of a thin slit. The slit shaped light beams which have passed through the slit aperture 106 are passed through a first objective lens 107 to a mirror 110 where the beams are reflected in a perpendicular direction to a second objective lens 108. The light beams which have passed through the second objective lens 108 are reflected by a half mirror 109 in a perpendicular direction to be projected along a projecting optical axis Oo to a patient's eye. In the projecting optical path 10a, a filter 111 is retractably provided.

The condenser lens 102 functions to produce an image of the filament of the tungsten lamp 101 at a space between electrodes of the xenon lamp 103. The condenser lens 104 functions to condense the light beams from the light sources into parallel beams. The first objective lens 107 has a front focal point at the location of the slit aperture 106 so that the light beams from the slit aperture 106 are made parallel by the lens 107. The second objective lens 108 focuses the light beams which have passed through the first objective lens 107 at the main crystalline lens of the patient's eye Et to form a slit image So. As in a conventional slit lamp, it is desirable to make the slit aperture adjustable with respect to the length and the width. It is also desirable to provide in the vicinity of the slit aperture 106 a rotatable disc having a plurality of circular apertures of different diameters so that a selected one of the circular apertures can be inserted into the projecting optical path to project a circular spot light at the front portion of the patient's eye. In the projecting optical path 10a, there is provided a polarizer 112 comprised of a polarized filter for the purpose which will be described later.

Crystalline Section Photographing Optical System 20

This optical system 20 includes an imaging lens 201, a retractable mirror 202 and a photographing film plane 203. The imaging lens 201 is arranged with its optical axis 20a intersecting obliquely the slit image So on the patient's eye Et and the photographing film plane 203 is also arranged obliquely with respect to the optical axis 20a. The imaging lens 201 and the film plane 203 are arranged so that the principal plane 201a of the lens 201 and an extension of the film plane 203 are intersected in a plane containing the slit image So. With this arrangement, it is possible to make the crystalline section image $S_1$ formed on the film plane focused substantially throughout the section.

The retractable mirror 202 is arranged in front of the film plane 203 and normally inserted into the photographing optical path as shown by solid lines in FIG. 1 so that the light beams from the imaging lens 201 are reflected by the mirror 202 toward the observing optical system 40 along an optical axis 20b. The mirror 202 is retracted to the position shown by phantom lines when a photographing shutter (not shown) is released to allow the light beams from the imaging lens 201 to pass to the film plane 203.

Retroillumination Photographing Optical System 30

This optical system 30 includes an objective lens 301 having an optical axis $O_1$ aligned with the slit light projecting optical axis Oo. A reticle 302 is provided along the optical axis $O_1$ so that the light beams from the objective lens 301 are focused at the reticle 302. The light beams from the reticle 302 are reflected by a mirror 303 and passed through relay lenses 304 and 307 to a retractable mirror 202. The light beams from the relay lens 307 are reflected, when the mirror 202 is in the retracted position shown in FIG. 1, by the mirror 202 toward the film plane 203 to form an overall image of the crystalline lens on the film plane 203.

Between the relay lenses 304, 307, there is provided an analyzer 306 which is comprised of a polarizer. The analyzer 306 is arranged with its polarizing axis perpendicular to that of the polarizer 112 so that it can block the reflection at the cornea of the patient's eye of the projection light from being passed to the film plane. Behind the relay lens 304, there is provided a half mirror 305 which functions to reflect a part of the light beams from the relay lens 304 toward the observing optical system 40.

Observing Optical System 40

Figure 3:
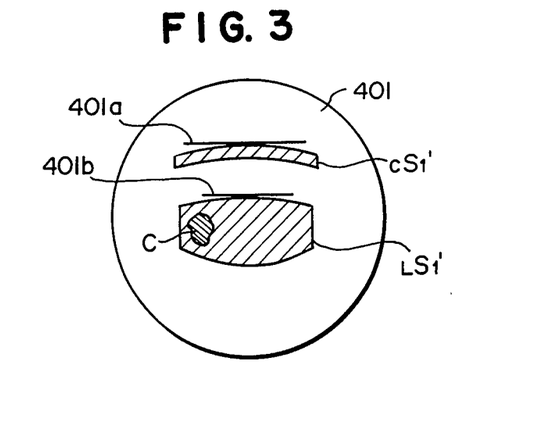
FIG. 3 is a diagrammatical view of the rotatable reticle provided in the eyepiece.

This optical system 40 includes a reticle 401 arranged on a reflecting optical axis 20b of the retractable mirror 202. The reticle 401 is positioned in conjugate with the film plane 203 and has mark lines 401a and 401b as shown in FIG. 3. When the mirror 202 is in the position shown by the solid lines, there is produced on the reticle 401 a crystalline section image $S_1'$ corresponding to the slit image So on the patient's eye Et. A mirror 402 is provided in the optical axis 20b and functions to reflect the light beams through the optical axis 20b in the direction along an observing optical axis $O_2$.

The observing optical axis $O_2$ is coaxial with the optical axis $O_1$ of the objective lens 301. A relay lens 403 and a rotatable reticle 404 are arranged along the optical axis $O_2$. The relay lens 403 has a principal plane which contains an intersection of the planes of the reticles 401 and 404 so that the crystalline section image $S_1'$ on the reticle 401 is relayed to the reticle 404 without destroying the focused condition. For the purpose of observing the image on the reticle 404, there is provided an eyepiece 405.

A relay lens 406 is provided in a reflecting optical path of the half-mirror 305 in the optical system 30 and the light beams which have passed through the relay lens 406 are reflected by a mirror 407 toward the optical axis $O_2$. A half-mirror 408 is arranged on the optical axis $O_2$ so that the light beams from the mirror 407 are reflected toward the rotatable reticle 404 to produce on the reticle 404 an image of the patient's eye. In the reflecting optical path of the half-mirror 305, there is also provided retractably an analyzer 409 which is similar to the analyzer 306. The optical system 40 further includes a shutter 410 for directing one of the light from the reticle 401 and the light from the half-mirror 305 alternately to the reticle 404.

Mark Projecting System

Figures 5, 6:
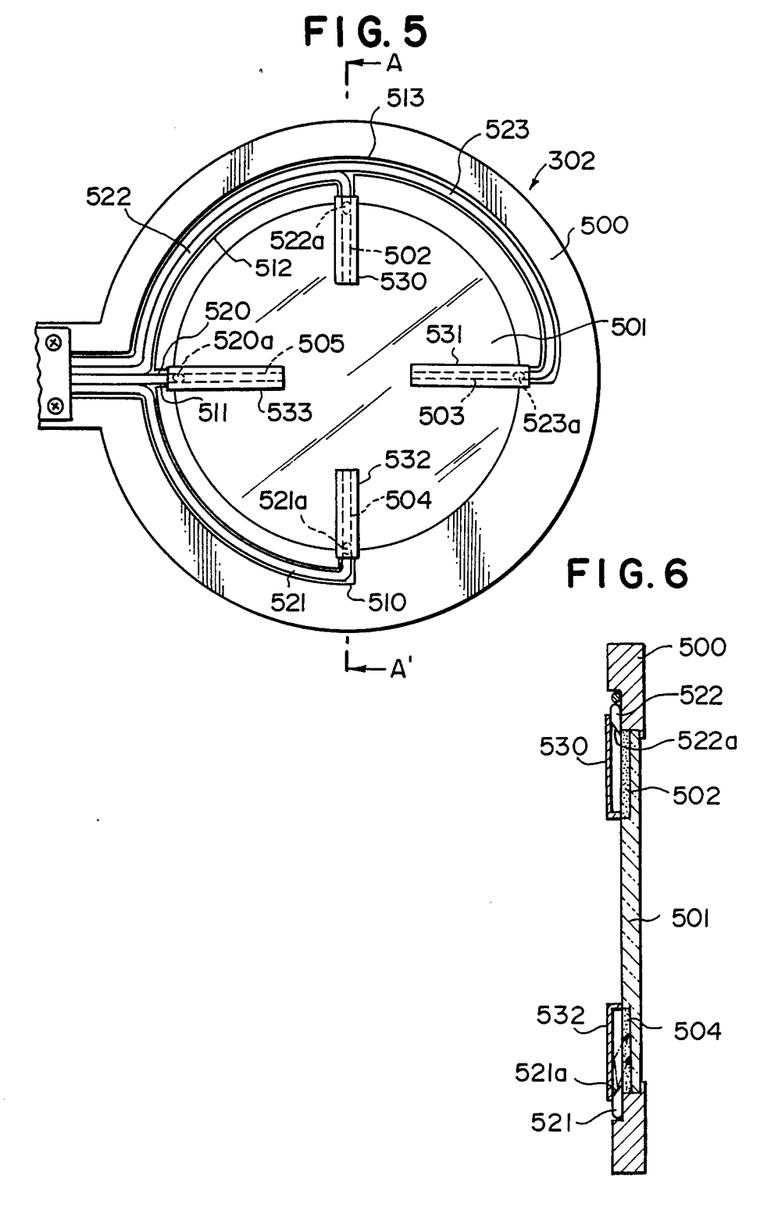
FIG. 5 is a front view showing the reticle in the optical system for the retroillumination method.
FIG. 6 is a sectional view taken along the line A—A in FIG. 5.

As shown in FIGS. 5 and 6, the reticle 302 comprises a frame 500 and a transparent glass plate 501 secured to the frame 500. The glass plate 501 has mark grooves 502, 503, 504 and 505 formed at 90° angular spacings. Covers 530, 531, 532 and 533 of semi-circular cross-section are provided respectively on the mark grooves 502, 503, 504 and 505. The covers have reflective inner surfaces.

The frame 500 is formed along its periphery with grooves 510, 511, 512 and 513 in which optical fibers 520, 521, 522 and 523 are respectively located. The optical fibers 520 through 523 have their emitting ends positioned in the mark grooves 502 through 505, respectively. The emitting end of each optical fiber is obliquely cut and arranged with the cut surface directed toward the cover. The optical fibers 520 through 523 are bundled together to form a fiber bundle 524 which is passed through the projecting optical system 10. The light injecting end of the fiber bundle 524 is divided into two parts 525 and 526, the part 525 being opposed to the xenon lamp 103 and the part 526 to the tungsten lamp 101. Between the part 526 and the tungsten lamp 101, there is a colored filter 540 having for example green color.

The light beams from the tungsten lamp 101 are passed through the filter 540 and the coloured light beams are then passed through the optical fibers to the emitting ends. Since the emitting ends of the optical fibers are obliquely cut, substantial part of the light beams are refracted toward the mark grooves 502 through 505 in the plate 501 and passed through the glass plate 501 toward the mirror 303 after being diffused by diffusion surfaces formed in the mark grooves. The light beams which have emitted from the optical fibers in the directions opposite to the mark grooves are reflected by the inner surfaces of the covers 530 through 533 toward the mark grooves.

Figure 7:
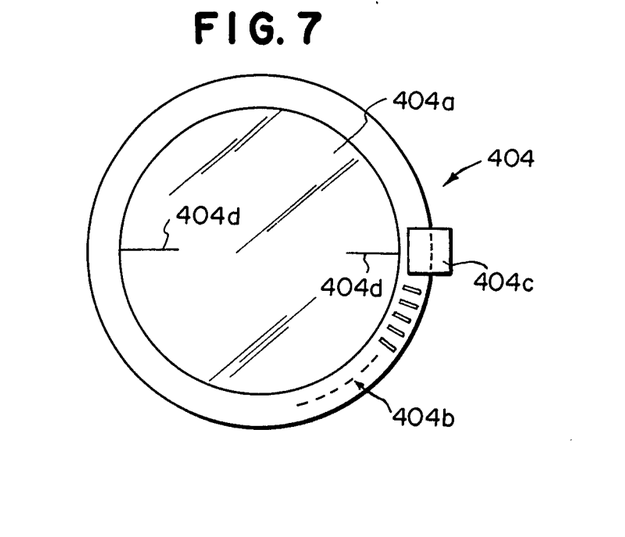
FIG. 7 is a front view of the rotatable reticle in the eyepiece.

As shown in FIGS. 1 and 7, the rotatable reticle 404 comprises an observing field 404a formed by a transparent glass plate having a pair of diametrically aligned mark lines 404d, an optical or magnetic code section 404b provided along the periphery of the observing field 404a, and a detecting head 404c for detecting the codes in the code section. The observing field 404a is rotatable about the observing optical axis $O_2$ whereas the detecting head 404c is secured to the barrel of the eyepiece. The detecting head 404c functions to detect the angle of rotation of the reticle 404 and the signals from the detecting head 404c are processed by a detecting circuit 1000 and the results of the detection are displayed by a displaying unit 1100. The output from the circuit 1000 is also applied through a controller 1200 to a data displaying head 1300 located in front of the film plane 203 so that a digital value of the angle of rotation of the reticle 404 is photographed.

Density Chart Photographing System 45

An shown in FIG. 1, an optical fiber 451 is provided with one end opposed to the xenon lamp 103 and the other end opposed to an optical system comprising a relay lens 452, an ND filter 453 and a density chart 454. The light beams which have passed through the density chart 454 are reflected by a mirror 456 and passed through an imaging lens 455 to the mirror 202. When the mirror 202 is in the retracted position, the light beams from the lens 455 are reflected by the mirror 202 to the film plane 203.

Housing 100 and the Support

As previously described, the aforementioned optical systems are contained in the housing 100 which is supported by a suitable support such as a U-shaped arm 5 for rotation about the coaxial optical axes $O_0$, $O_1$ and $O_2$. The eyepiece 405 and the detecting head 404c of the rotatable reticle 404 are secured to a stationary part of the support so that they are maintained stationary even when the housing 100 is rotated.

Operations

Figures 2A, 2B:
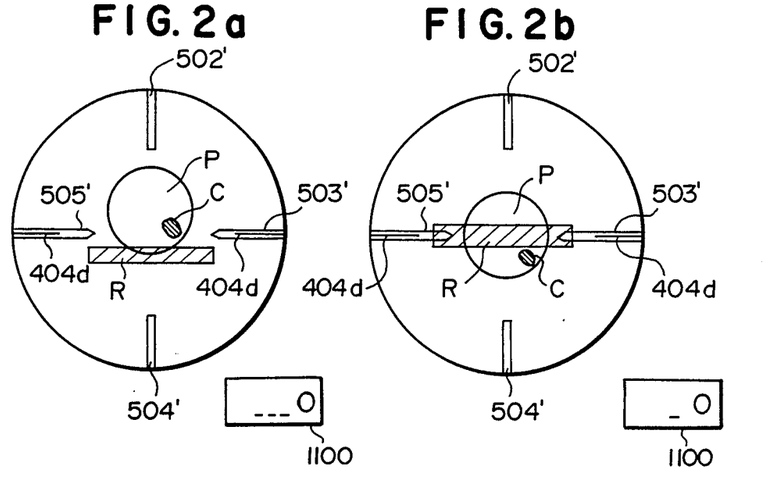
FIGS. 2a, 2b, 2c and 2d are views of the eyepiece showing the manner of using the instrument.

The shutter 410 is operated to select the retroillumination system and the analyzer 409 is then retracted from the optical path. Thereafter, the lamp 101 in the projecting optical system 10 is turned on to project the slit light through the slit aperture 106 to the patient's eye. A part of the light beams from the lamp 101 pass through the green filter 540 and the optical fiber bundle 524 to illuminate the mark grooves 502 through 505 in the reticle 302. Thus, the operator can observe images of cross lines 502', 503', 504' and 505' in the field of the eyepiece as shown in FIG. 2. Where the instrument is not sufficiently aligned with the patient's eye, the image P of the pupil of the eye is offset as shown in FIG. 2a from the image R which is produded by a reflection of the slit light projection at the cornea. Further, the images P and R are also offset from the images of the marks 502' through 505'. The support 5 is then adjusted so that the pupil image P is aligned with the center of the mark images 502' through 505' and the slit image R is aligned with the mark images 503' and 505' as shown in FIG. 2b.

Then, the analyzer 409 is inserted into the optical path. The reflection at the cornea of the projected slit light has a polarizing axis perpendicular to the polarizing axis of the analyzer 409 so that the reflection is blocked by the analyzer 409. The light beams reflected at the eye fundus are substantially de-polarized due to the diffusion at the eye fundus so that the cystalline lens is illuminated by the light beams reflected at the eye fundus. Thus, the crystalline lens of the patient's eye can be observed without being blocked by the analyzer 409. The image of the crystalline lens can be focused by an adjustment of the support.

Figure 2C:
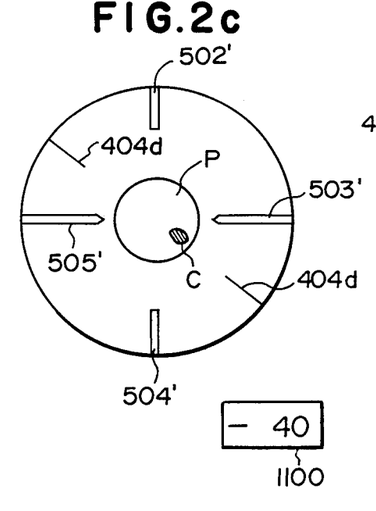
Figure 2D:
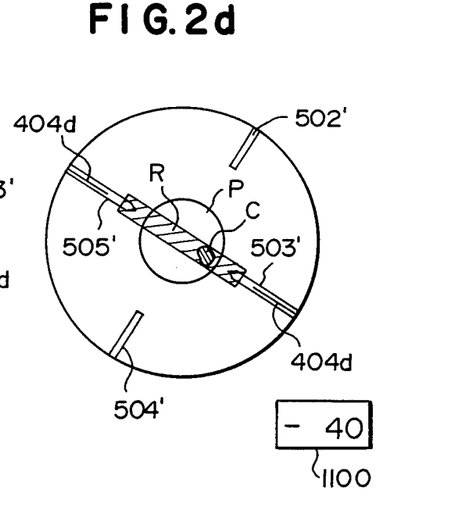

When it is desired to inspect the section of a diseased portion, for example, the portion shown by C in FIG. 2, the rotatable reticle 404 is rotated until the mark lines 404d are aligned with a diametrical line passing through the diseased portion C as shown in FIG. 2c. Then, the analyzer 409 is retracted from the optical path so that the slit image R is displayed on the reticle 404. The housing 100 is then rotated until the slit image R and the mark images 503' and 505' are aligned with the mark lines 404d as shown in FIG. 2.

The shutter 410 is then actuated to select the optical path from the optical system 20. The image of the section of the crystalline lens is formed at first on the reticle 401 by the imaging lens 201. The reticle 401 if formed with mark lines 401a and 401b as shown in FIG. 3. Confirmations are then made as to whether the front end of the cornea image $C^S1'$ is aligned with the mark line 401a and as to whether the lens section image $L^S1'$ is aligned with the mark line 401b. Accurate alignment can be made by a movement of the housing 100. The lens section image $L^S1'$ is relayed to the reticle 404 through the mirror 402, the relay lens 403 and the half mirror 408 to produce an image $S_1''$ which can be observed through the eyepiece.

Figure 4:
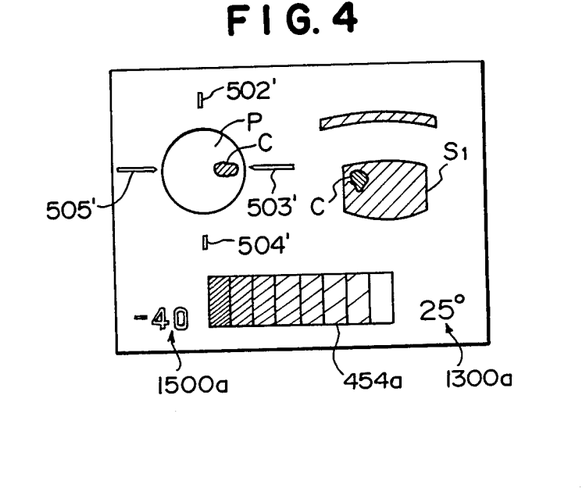
FIG. 4 shows an example of the photograph taken by the instrument.

For photographing, a shutter release switch (not shown) is actuated to retract the mirror 202 and energize the xenon lamp 103. By retracting the mirror 202, the lens section photographing path is opened so that the lens section image $S_1$ is photographed on the film plane 203 as shown in FIG. 4. At the same time, the light beams from the optical system 30 are passed through the half-mirror 305 and the analyzer 306 to the mirror 202 where the light beams are reflected toward the film plane 203 to produce an image of the crystalline lens as well as the mark images 502' through 505' on the film plane 203.

The grooves 502 through 505 are rotated together with the housing 100 so that the images 502' through 505' are photographed in predetermined positions on the film plane 203. However, the image of the crystalline lens is rotated with respect to the mark images 502' through 505' so that the diametrical line aligned with the mark lines 503' and 505' represent the location where the lens section image is photographed. On the film plane 203, there are further photographed a digital values 1300a and 1500a respectively designating the angles of rotations of the mark lines 404d and the rotatable reticle 404. There is further photographed a density chart 454a.

When it is desired to take pictures of the same lens section at predetermined time intervals for the purpose of recording progress of a certain disease such as cataract, the position of the reticle 404 is at first determined taking reference to the value 1500a which shows the position of the reticle 404 in the previously taken picture and then the housing 100 is rotated until the mark images 503' and 505' on the reticle 404 are aligned with the mark lines 404d. For the purpose, an indicator 1100 is provided to indicate the rotating angle of the reticle 404.

Alternative Embodiments

Figure 8A:
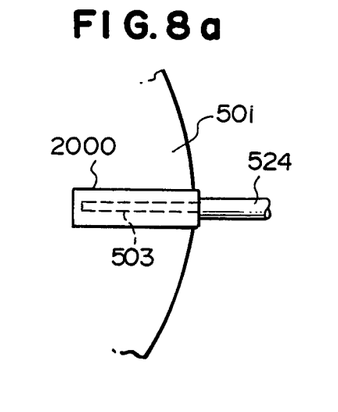
FIG. 8a is a fragmentary front view of the reticle in the optical system for the retroillumination method.
Figure 8B:
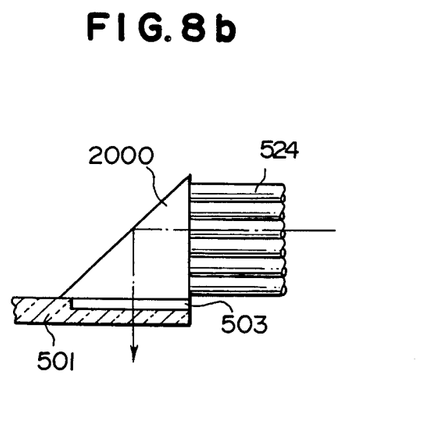

As shown in FIGS. 8a and 8b, a triangular prism 2000 may be attached to the glass plate 501 in the reticle 302 at the location of each of the grooves 502 through 505 and the emitting ends of the optical fibers 524 may be adhesively attached to one surface of the prism 2000. In this arrangement, the light beams from the optical fibers 524 are reflected at the slanted surface of the prism 2000 toward the groove.

The slit light illumination for observation may be made by infrared rays. Then, an image taking tube may be provided in lieu of the eyepiece so that the images can be displayed on a TV. The photographing film may then be substituted by a video recording apparatus. For retroillumination, any light beams other than slit light may be used.

The invention has thus been shown and described with reference to specific embodiments, however, it should be noted that the invention is in no way limited to the details of the illustrated structures but changes and modifications may be made without departing from the scope of the appended claims.

We claim:

1. An eye disease inspection instrument, comprising:
   a slit light projection optical system including a projection lens having a projection optical axis and a slit aperture for projecting a slit light flux to a fundus via a crystalline lens of a patient's eye, said projection lens forming an image of said slit aperture on the crystalline lens so as to cut optically the crystalline lens for forming an optical section thereof;
   a first observation optical system including a first objective lens having a first optical axis which intersects said projection optical axis for imaging an intermediate range of the optical section of the crystalline lens;
   a second observation optical system including a second objective lens having a second optical axis which is substantially coaxial with respect to a part of said projection optical axis, said second observation optical system being arranged for imaging an intermediate image of a retroillumination image of the crystalline lens resulting from illumination of the crystalline lens from the back of the light flux reflected at the fundus of the patient's eye;
   ocular means positioned for observing both the intermediate images of the optical section and the retroillumination image;
   optical path selection means positioned for alternately selecting one of the first and second observation optical systems for observation by said ocular means;
   said slit light projection optical system including a polarizer having a first polarization axis; and
   said second observation optical system including an analyzer which has a second polarization axis lying perpendicular to the first polarizing axis and which is retractable from an optical path of said second observation optical system.

2. An instrument in accordance with claim 1, wherein said second observation optical system includes a reticle disposed on said second optical axis and at the position whereat the intermediate range image is formed and said reticle has a mark for designating a position of incidence of the slit light flux on the crystalline lens.

3. An instrument in accordance with claim 2, wherein said first observation optical system, said slit light projection optical system and said reticle of said second observation optical system are rotatable about said part of said projecting optical axis.

4. An instrument in accordance with claim 1, wherein said first objective lens has a principal plane which intersects an extension of an image plane wherein the intermediate image of the crystalline lens is formed by said first objective lens on a line of intersection between said extension of the image plane and an extension of a plane containing the optical section of the crystalline lens.

5. An eye disease inspection instrument, comprising:

a slit light projection optical system including a projection lens having a projection optical axis and a slit aperture being positioned for projecting a slit light flux to a fundus via a crystalline lens of a patient's eye, said projection lens forming an image of said slit aperture on the crystalline lens so as to cut optically the crystalline lens for forming an optical section, thereof;

a first recording optical system including a first imaging lens having a first optical axis which intersects said projecting optical axis, said first recording optical system being positioned for imaging an image of the optical section of the crystalline lens on one part of a sensitive plane of a recording medium;

a second recording optical system including a second imaging lens having a second optical axis which is substantially coaxial with respect to a part of said projection optical axis, said second recording optical system being positioned for imaging an image of a retroillumination image of the crystalline lens resulting from illumination of the crystalline lens from the back of the light flux reflected at the fundus of the patient's eye on another part of said image take-up plane of said recording medium;

said slit light projection optical system including a polarizer having a first polarizing axis; and said second recording optical system including a first analyzer having a second polarizing axis which is perpendicular to the first polarizing axis of said polarizer.

6. An instrument in accordance with claim 5, wherein said second recording optical system includes optical path dividing means which is disposed between said second imaging lens and said first analyzer and which divides a light flux from said second imaging lens into one part sent to said recording medium and another part sent to a second observation optical system which is connected optically with said optical path dividing means and which is used for observing said retroillumination image of the crystalline lens.

7. An instrument in accordance with claim 5, wherein said first recording optical system includes optical path selection means disposed therein for alternatively switching a light flux from said first imaging lens to said recording medium and to a first observation optical system, which is connected optically with said optical path selection means and which is used for observing the optical section of the crystalline lens.

8. An instrument in accordance with claim 6, wherein said optical path dividing means is a half mirror for transmitting one part of said light flux toward said recording medium and for reflecting another part of said light flux toward said second observation optical system.

9. An instrument in accordance with claim 7, wherein said optical path selection means is a retractable mirror which can alternatively be inserted into and retracted from an optical path of said first recording optical system, and whereby said retractable mirror transmits the light flux from said first imaging lens to said recording medium when said retractable mirror is retracted and said retractable mirror reflects said light flux from said first imaging lens to said first observation optical system when said retractable mirror is inserted.

10. An instrument in accordance with either of claims 6 and 7, wherein said first and second observation optical system includes one common ocular lens which has an optical axis coaxial with said part of said projection optical axis and which is used for observing said optical section and said retroillumination image of the crystalline lens.

11. An instrument in accordance with claim 5, wherein said second imaging lens forms an intermediate image of the retroillumination image and wherein said second recording optical system includes a reticle at a position whereat the intermediate image is formed and said reticle has mark means for indicating a location of the optical section of the crystalline lens which is illuminated by the slit light flux.

12. An instrument in accordance with claim 11, wherein said first and second recording optical system, said slit light projection optical system and said reticle are rotatable together about said part of said projection optical axis.

13. An instrument in accordance with claim 10, wherein said second imaging lens forms an intermediate image of the retroillumination image, wherein said second recording optical system includes a reticle at a position whereat the intermediate image is formed and said reticle has mark means for indicating a location of the optical section of the crystalline lens which is illuminated by the slit light flux, and wherein said first and second recording optical system, said first and second observation optical system and said reticle are rotatable together about said part of said projection optical axis.

14. An instrument in accordance with claim 5, wherein said first imaging lens of said first recording optical system has a principal plane which intersects an extension of said image take-up plane on a line of intersection between said extension of said image take-up plane and an extension of a plane containing the optical section of the crystalline lens.

15. An instrument in accordance with claim 5, wherein said recording medium is photographing means, wherein said image take-up plane is a photosensitive layer of a photographic film and wherein the image of the optical section and the image of the retroillumination image of the crystalline lens are photographed in different areas of one frame of said photographic film.

16. An instrument in accordance with claim 6, wherein said second observation optical system includes a second analyzer disposed retractably therein and having a third polarizing axis which is perpendicular to the first polarizing axis of said polarizer.

17. An instrument in accordance with either of claims 6 and 7, wherein said first and second observation optical system includes one common ocular lens which has an optical axis coaxial with said part of said projection optical axis and which is used for observing said optical section or said retroillumination image of the crystalline lens.

* * * * *